United States Patent [19]

Teulon

[11] 4,271,161
[45] Jun. 2, 1981

[54] INDANE-ACETIC ACID AMINOESTERS, THEIR PREPARATION AND THEIR USE IN THERAPY

[75] Inventor: Jean M. Teulon, La Celle Saint Cloud, France

[73] Assignee: Hexachimie, France

[21] Appl. No.: 55,907

[22] Filed: Jul. 9, 1979

[30] Foreign Application Priority Data

Jul. 24, 1978 [FR] France .................... 78 21849
May 28, 1979 [FR] France .................... 79 13532

[51] Int. Cl.³ .................. C07D 295/10; C07D 295/08
[52] U.S. Cl. ...................................... 424/250; 544/394
[58] Field of Search ..................... 544/394; 424/250

[56] References Cited

U.S. PATENT DOCUMENTS

| 3,953,449 | 4/1976 | Giudicelli et al. | 544/394 |
| 4,093,724 | 6/1978 | Allais et al. | 544/394 |
| 4,147,790 | 4/1979 | Allais et al. | 544/394 |

FOREIGN PATENT DOCUMENTS 2260334  9/1975  France .

*Primary Examiner*—Jose Tovar

*Attorney, Agent, or Firm*—Poms, Smith, Lande & Rose

[57] ABSTRACT

Compounds of the formula:

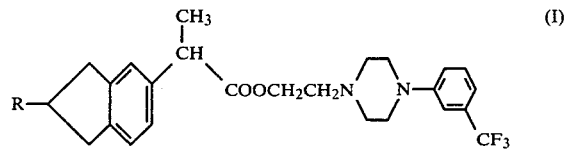

(I)

in which R represents an ethyl or isopropyl group, and their addition salts with acids or quaternary ammonium salts can be prepared from the compounds:

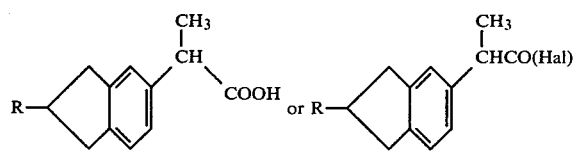

in which R has the same meaning as above, and are valuable as analgesics.

8 Claims, No Drawings

INDANE-ACETIC ACID AMINOESTERS, THEIR PREPARATION AND THEIR USE IN THERAPY

The present invention relates to new indane aminoesters, the process for their preparation and their application in therapy.

These new derivatives correspond to the general formula:

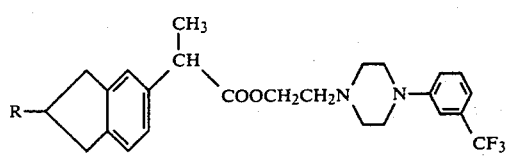

in which R is an ethyl or isopropyl group.

The invention also relates to the addition salts of the compounds of the formula I, namely addition salts with acids or quaternary ammonium salts.

The addition salts with acids are obtained by reaction with an inorganic or organic acid in accordance with a method which is in itself known.

Amongst the acids which can be used for this purpose, there may be mentioned, in particular, hydrochloric, sulphuric, phosphoric, oxalic, succinic, methanesulphonic, cyclohexylsulphamic, formic, aspartic, glutamic, N-acetylaspartic, N-acetylglutamic, ascorbic, maleic, malic, fumaric, lactic, benzoic, cinnamic and p-toluenesulphonic acids.

The new compounds according to the invention possess valuable pharmacological actions and can be useful in therapy as analgesic agents.

According to the invention, therapeutic compositions are proposed which are useful, in particular, for the treatment of pain and are characterised in that they contain, in association with a physiologically acceptable excipient, an effective amount of at least one compound of the formula I or one of its non-toxic addition salts In order to prepare a compound of the formula I, several methods are available which apply known principles. One process of preparation is as follows:

(a) the halides (III) of the acids of the formula II

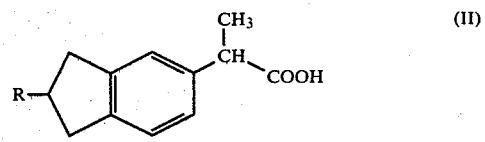

in which R has the same meaning as above, are reacted with the aminoalcohol of the formula:

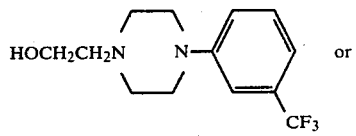

(b) the inorganic salts (IV) of the acids of the formula II are reacted with a halide of the formula:

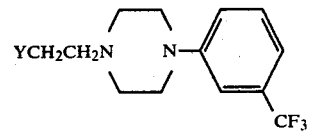

in which Y is a halogen atom.

The steps of the process according to the invention are illustrated in the following scheme:

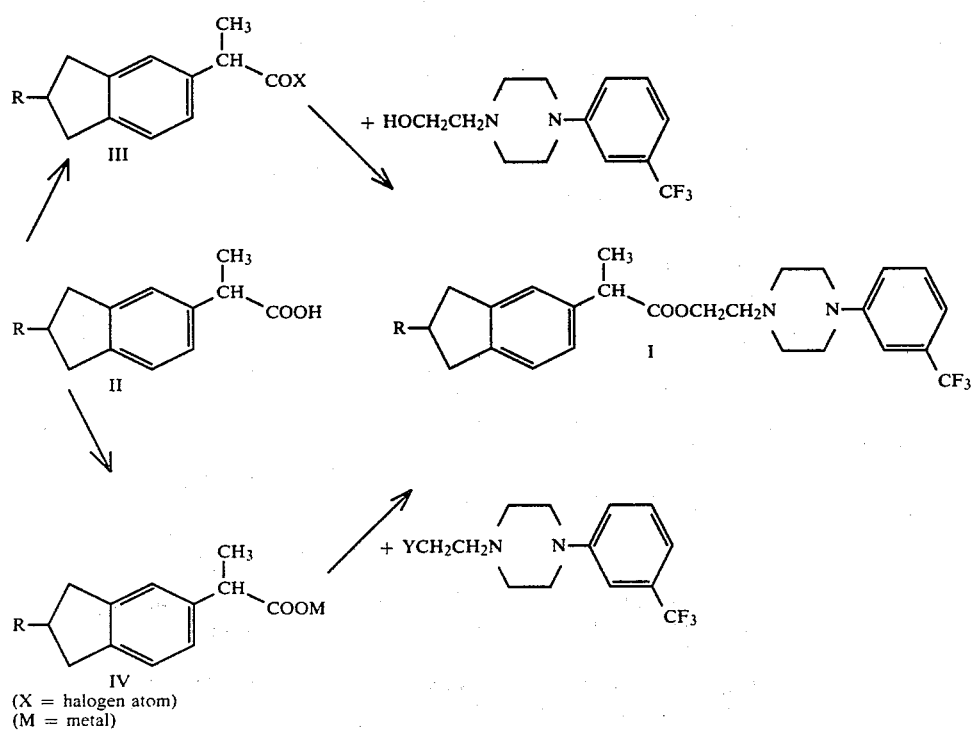

(X = halogen atom)
(M = metal)

In order to prepare the compounds of the formula I, it is also possible to use the method illustrated by the following scheme:

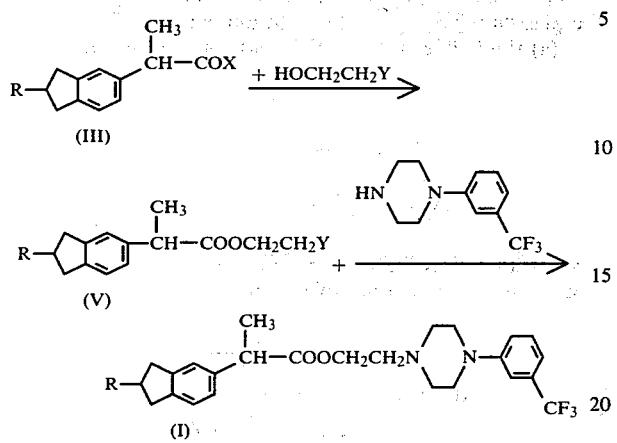

in which: R is an ethyl or isopropyl group and X and Y are halogen atoms.

(a) The acid halides of the formula III are reacted with a halogenoalcohol HOCH₂CH₂Y in an organic solvent, such as acetone, chloroform, methylene chloride or an aromatic hydrocarbon, in the presence or absence of a base such as pyridine or triethylamine, and (b) the resulting halogenoester of the formula V is reacted with m-trifluoromethylphenylpiperazine:

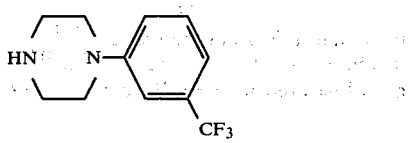

in an organic solvent, such as acetone, chloroform, methylene chloride or an aromatic hydrocarbon, using either twice the amount of m-trifluoromethylphenylpiperazine or a tertiary nitrogen-containing base such as triethylamine.

The halide of the formula (V) is new and forms part of the invention.

The invention is illustrated below by non-limiting synthesis examples:

EXAMPLE 1

2-Methyl-(2-ethylindan-5-yl)-acetic acid chloride

A solution of 57 g of 2-methyl-(2-ethylindan-5-yl)acetic acid and 40 ml of thionyl chloride in 200 ml of benzene is heated under reflux for 2 hours. The solvent and the excess thionyl chloride are then evaporated off in vacuo. The resulting oil is then distilled in vacuo. 56 g of 2-methyl-(2-ethylindan-5-yl)-acetic acid chloride are thus recovered in the form of a liquid:

Boiling point (1 mm Hg)=125°–128° C.

EXAMPLE 2

2-Methyl-(2-ethylidan-5-yl)-acetic acid (m-trifluoromethylphenyl)-piperazinoethyl ester hydrochloride 63 ml of triethylamine are added dropwise to 64 g of (m-trifluoromethylphenyl)-piperazinoethanol hydrochloride in 600 ml of anhydrous benzene.

After the addition is complete, the mixture is stirred for 30 minutes at ambient temperature and 55.9 g of the 2-methyl-(2-ethylidan-5-yl)-acetic acid chloride prepared in Example 1, in 100 ml of benzene, are then added dropwise.

After the addition is complete, the reaction mixture is heated under reflux for 5 hours.

After cooling, the organic phase is washed carefully with water, with a 5% strength solution of sodium hydroxide in the presence of ice, and then again with water, and dried over sodium carbonate. After evaporating off the benzene, the residue, which is in the form of a liquid, is dissolved in acetone, and a solution of hydrogen chloride in ether is added until the pH is acid. The crystals formed are filtered off and washed carefully with acetone. 70 g of 2-methyl-(2-ethylidan-5-yl)-acetic acid (m-trifluoromethylphenyl)-piperazinoethyl ester hydrochloride are thus isolated in the form of white crystals having a melting point of 199°–201° C.

EXAMPLE 3

2-Methyl-(2-isopropylidan-5-yl)-acetic acid chloride

By following the procedure of Example 1, but using 31 g of 2-methyl-(2-isopropylidan-5-yl)-acetic acid, 30 g of 2-methyl-(2-isopropylindan-5-yl)-acetic acid chloride are recovered in the form of a liquid:

Boiling point (1 mm Hg)=150° C.

EXAMPLE 4

2-Methyl-(2-isopropylidan-5-yl)-acetic acid (m-trifluoromethylphenyl)-piperazinoethyl ester A solution of 6.9 g of the 2-methyl-(2-isopropylindan-5-yl)-acetic acid chloride prepared in Example 3, in 20 ml of benzene, is added dropwise to a solution of 7.5 g of (m-trifluoromethylphenyl)-piperazinoethanol and 4.5 ml of triethylamine in 100 ml of benzene.

After the addition is complete, the reaction mixture is heated under reflux for 5 hours.

After cooling, the organic phase is washed carefully with water and dried over sodium carbonate and the benzene is evaporated off in vacuo. The resulting residue is taken up in cold pentane. The crystals formed are filtered off and washed with pentane. 11 g of 2-methyl(2-isopropylidan-5-yl)-acetic acid (m-trifluoromethylphenyl)piperazinoethyl ester are thus isolated in the form of white crystals having a melting point of 56°–58° C.

EXAMPLE 5

2-Methyl-(2-ethylindan-5-yl)-acetic acid (m-trifluoromethylphenyl)-piperazinoethyl ester hydrochloride 21.8 g of 2-methyl-(2-ethylindan-5-yl)-acetic acid are treated with a solution of sodium methylate, prepared from 2.3 g of sodium dissolved in 40 ml of methanol. After evaporating off the solvent, the sodium salt of the acid is obtained in the form of a white powder.

A solution of this sodium salt and 29.3 g of β-[(m-trifluoromethylphenyl)-piperazino]-chloroethane in 100 ml of xylene is heated under reflux for 7 hours.

After cooling the reaction mixture, the organic phase is washed with water and dried over sodium carbonate. After evaporating off the solvent, the base is isolated in the form of a liquid.

This base is taken up in acetone, and a solution of hydrogen chloride in ether is added until the pH is acid.

The resulting crystals are washed carefully with acetone and dried. 36 g of 2-methyl-(2-ethylindan-5-yl)-acetic acid (m-trifluoromethylphenyl)-piperazinoethyl ester hydrochloride are thus recovered in the form of white crystals having a melting point of 200°-2° C.

EXAMPLE 6

2-Methyl-(2-isopropylindan-5-yl)-acetic acid (m-trifluoromethylphenyl)-piperazinoethyl ester By following the procedure of Example 5, but using 23.2 g of 2-methyl-(2-isopropylindan-5-yl)-acetic acid, 37 g of 2-methyl-(2-isopropylindan-5-yl)-acetic acid (m-trifluoromethylphenyl)-piperazinoethyl ester, as the base, are recovered in the form of white crystals having a melting point of 56°-58° C.

EXAMPLE 7

2-Methyl-(2-ethylindan-5-yl)-acetic acid bromoethyl ester

Formula V: R=ethyl, Y=Br

Method A

A solution of 4.4 g of 2-methyl-(2-ethylindan-5-yl)acetic acid chloride and 2.45 g of 2-bromoethanol in 50 ml of anhydrous acetone is heated under reflux for 4 hours.

After evaporating off the solvent, the resulting oily residue is dissolved in ether and the ether solution is washed, in the presence of ice, with an aqueous solution of sodium bicarbonate and with water and is then dried over sodium sulphate. After filtering and evaporating off the solvent, 5.9 g of 2-methyl-(2-ethylindan-5-yl)-acetic acid bromoethyl ester are obtained in the form of an oily residue which is used in the crude state for the following step.

Method B

A solution of 12 g of 2-methyl-(2-ethylindan-5-yl)acetic acid chloride in 15 ml of chloroform is added, at 0° C., to a solution of 6.4 g of 2-bromoethanol and 5.5 ml of pyridine in 30 ml of chloroform.

After the addition is complete, the reaction mixture is heated under reflux for 1 hour.

After cooling, the reaction mixture is washed with water, with 5% strength hydrochloric acid and then again with water. The chloroform phase is dried and, after evaporating off the solvent, the oily residue is distilled in vacuo. 13.7 g of 2-methyl-(2-ethylindan-5-yl)acetic acid bromoethyl ester are thus recovered in the form of an oil.

Boiling point (0.2 mm Hg)=138°-148° C.

EXAMPLE 8

2-Methyl-(2-ethylindan-5-yl)-acetic acid m-trifluoromethylphenylpiperazinoethyl ester hydrochloride formula I: R=ethyl

Method A

A solution of 5.9 g of 2-methyl-(2-ethylindan-5-yl)acetic acid bromoethyl ester obtained by method A of Example 7, in 15 ml of anhydrous acetone, is added to a solution of 4.2 g of m-trifluoromethylphenylpiperazine and 3 ml of triethylamine in 25 ml of anhydrous acetone.

The reaction mixture is stirred for 2 hours at ambient temperature and then heated under reflux for 6 hours.

After cooling, the triethylamine hydrobromide formed is filtered off and the filtrate is concentrated in vauo.

The resulting residue is taken up in ether and the mixture is again filtered.

The new filtrate recovered is concentrated in vacuo. 9.8 g of oil are thus obtained.

This oil is dissolved in 50 ml of acetone, 25 ml of water are then added and the mixture is acidified to pH 3 with concentrated hydrochloric acid.

The crystals formed are filtered off, washed with water and then with acetone and dried.

2.7 g of 2-methyl-(2-ethylindan-5-yl)-acetic acid m-trifluoromethylphenylpiperazinoethyl ester hydrochloride are thus recovered in the form of white crystals having a melting point of 201°-203° C.

Method B

A solution of 13.6 g of the 2-methyl-(2-ethylindan-5-yl)-acetic acid bromoethyl ester prepared in Example 7 by method B, 9.6 g of m-trifluoromethylphenylpiperazine, 7 ml of triethylamine and 200 mg of sodium iodide, in 100 ml of anhydrous benzene, is heated under reflux for 10 hours.

The reaction mixture is cooled, washed carefully with water and dried over sodium sulphate and the benzene is evaporated off in vacuo.

The resulting oily residue, weighing 20 g, is taken up in 60 ml of acetone, and 3.5 ml of concentrated hydrochloric acid, and then 40 ml of water, are added in the cold.

The crystals formed are filtered off, washed with a small amount of water and then with acetone and dried.

14.2 g of 2-methyl-(2-ethylindan-5-yl)-acetic acid n-trifluoromethylphenylpiperazinoethyl ester hydrochloride are thus recovered in the form of white crystals having a melting point of 202°-203° C.

EXAMPLE 9

2-Methyl-(2-isopropylindan-5-yl)-acetic acid bromoethyl ester formula V: R=isopropyl, Y=Br

Method A

A solution of 32 g of 2-methyl-(2-isopropylindan-5-yl)-acetic acid chloride in 25 ml of chloroform is added, at 0° C., to a solution of 16 g of 2-bromoethanol and 14 ml of pyridine in 50 ml of chloroform.

After the addition is complete, the reaction mixture is heated under reflux for 1 hour.

After cooling, the reaction mixture is washed with water, with 5% strength hydrochloric acid and then again with water.

The chloroform phase is dried out, after evaporating off the solvent, the oily residue, weighing 49 g, is distilled in vacuo. 35.2 g of 2-methyl-(2-isopropylindan-5-yl)-acetic acid bromoethyl ester are thus recovered in the form of an oil.

Boiling point (1.5 mm Hg)=165°-175° C.

Method B

A solution of 32 g of 2-methyl-(2-isopropylindan-5-yl)-acetic acid chloride in 25 ml of acetone is added dropwise to a solution of 16 g of 2-bromoethanol and 10.4 ml of pyridine in 125 ml of acetone.

After the addition is complete, the reaction mixture is heated under reflux for 1 hour 30 minutes.

The reaction mixture is then concentrated in vacuo, the residue is taken up in ether and the resulting mixture is washed with water, with 5% strength hydrochloric acid and then again with water. The ether phase is dried and the solvent is evaporated off in vacuo.

40 g of 2-methyl-(2-isopropylindan-5-yl)-acetic acid bromoethyl ester are thus recovered in the form of an oil which is used in the crude state for the following operations.

EXAMPLE 10

2-Methyl-(2-isopropylindan-5-yl)-acetic acid m-trifluoromethylphenylpiperazinoethyl ester hydrochloride formula I: R=isopropyl

Method A

A solution of 35.2 g of the 2-methyl-(2-isopropylindan-5-yl)-acetic acid bromoethyl ester prepared in Example 9 by method A, 47.8 g of m-trifluoromethylphenylpiperazine and 1 g of sodium iodide, in 300 ml of anhydrous toluene, is heated under reflux for 8 hours.

The reaction mixture is cooled and the m-trifluoromethylphenylpiperazine hydrobromide is filtered off and washed with benzene.

The organic filtrate is washed with water and then dried and concentrated in vacuo.

The resulting oily residue, weighing 61.7 g, is taken up in 250 ml of acetone, and 8.7 ml of concentrated hydrochloric acid, and then 150 ml of water, are added in the cold.

The resulting crystals are filtered off, washed with a small amount of water and then acetone and dried.

35.7 g of 2-methyl-(2-isopropylindan-5-yl)-acetic acid m-trifluoromethylphenylpiperazinoethyl ester hydrochloride are thus recovered in the form of white crystals having a melting point of 191°-193° C.

Method B

A solution of 40 g of the 2-methyl-(2-isopropylindan-5-yl)-acetic acid bromoethyl ester prepared in Example 9 by method B, 31.5 g of m-trifluoromethylphenylpiperazine hydrochloride and 36.5 ml of triethylamine, in 200 ml of acetone, is heated under reflux for 8 hours.

The reaction mixture is then concentrated in vacuo, the residue is taken up in a mixture of water and ice and the resulting mixture is extracted with ether. The ether phase is washed with water, dried over sodium sulphate and then concentrated in vacuo.

The resulting residue, weighing 57 g, is taken up in 150 ml of acetone, and 10 ml of concentrated hydrochloric acid, and then 100 ml of water, are added. The crystals formed are filtered off, washed with a small amount of water and then acetone and dried.

27.4 g of 2-methyl-(2-isopropylindan-5-yl)-acetic acid m-trifluoromethylpiperazinoethyl ester hydrochloride are thus recovered in the form of white crystals having a melting point of 193°-194° C.

Method C

A solution of 32 g of 2-methyl-(2-isopropylindan-5-yl)-acetic acid chloride in 25 ml of chloroform is added dropwise to a solution of 16 g of 2-bromoethanol and 14 ml of pyridine in 50 ml of chloroform, whilst cooling with ice.

After the addition is complete, the reaction mixture is allowed to return to ambient temperature and then heated under reflux for 1 hour.

The reaction mixture is then allowed to return to ambient temperature and 19.6 ml of triethylamine and 29.5 g of m-trifluoromethylphenylpiperazine are added.

The reaction mixture is then heated under reflux for 12 hours.

After cooling, it is diluted with chloroform and the resulting mixture is washed carefully with water.

The chloroform phase is dried and the solvent is evaporated off in vacuo.

The resulting residue, weighing 50.7 g, is taken up in 150 ml of acetone, and 8.5 ml of concentrated hydrochloric acid and 100 ml of water are then added.

The resulting crystals are filtered off, washed with a small amount of water and then with acetone and dried.

27.3 g of 2-methyl-(2-isopropylindan-5-yl)-acetic acid m-trifluoromethylphenylpiperazinoethyl ester hydrochloride are thus recovered in the form of white crystals having a melting point of 193°-194° C.

Pharmacological results relating to the two new indane aminoesters of the formula I, according to the invention, will be found below and demonstrate:

(A) their analgesic action:

The products being tested are administered orally (p.o.) to batches of 12 male mice (SPF, strain $OF_1$), weighing 19–20 g. After one hour, 0.3 ml/mouse of a 0.02% strength solution of phenylbenzoquinone is injected intraperitoneally and the number of pain reactions (abdominal writhing) is counted from the 5th to the 10th minute after the latter treatment.

The table below gives the percentage inhibition of these reactions.

| $mg.kg^{-1}$ p.o. | Example 2 or 5 | Example 4 or 6 |
| --- | --- | --- |
| 1 | 22 | |
| 2 | 47 | |
| 4 | 59 | |
| 8 | 64 | 23 |
| 16 | 65 | 40 |
| 32 | 82 | 67 |
| 64 | | 75 |
| 128 | | 75 |
| $ED_{50}$ $mg.kg^{-1}$ p.o. | 4 | 25 |

(B) their toxicity:

In mice, no mortality was observed after intraperitoneal administration up to doses of:

512 $mg.kg^{-1}$ for Examples 2 or 5, and
256 $mg.kg^{-1}$ for Examples 4 or 6.

The compounds (I) according to the invention therefore possess analgesic properties and have a very low toxicity.

They can therefore be used in human therapy, in the form of tablets or sugar-coated pills containing a dose of 100 to 200 mg, or in the form of suppositories containing a dose of 300 to 500 mg, for treating acute and chronic pain of various origins. The daily posology for an adult can be from about 0.5 to 2 g of active ingredient.

I claim:

1. Indane esters of the formula (I):

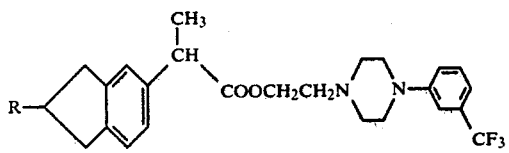 (I)

in which R represents an ethyl or isopropyl group and their addition salts with acids.

2. Compounds according to claim 1 which are hydrochlorides.

3. The compound of formula

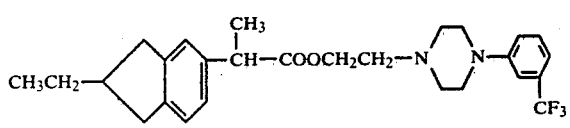

4. The compound of formula

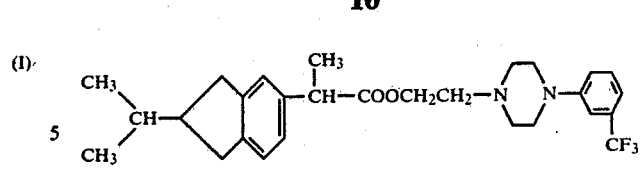

5. A pharmaceutical composition comprising an analgesic effective amount of a compound claimed in claim 1 together with a pharmaceutically acceptable carrier.

6. A composition according to claim 5, in the form of tablets or pills each containing 100 to 200 mg of active ingredient or in the form of suppositories each containing 300 to 500 mg of active ingredient.

7. A method of relieving pain in a patient which comprises administering to the patient an effective daily dose of a compound claimed in claim 1.

8. A method according to claim 7, in which the daily dose for an adult patient is 0.5 to 2 g of active ingredient.